United States Patent [19]

Korver, II

[11] Patent Number: 5,537,454
[45] Date of Patent: Jul. 16, 1996

[54] RADIATION THERAPY GRID FOR USE WITH TREATMENT COUCH

[75] Inventor: Clayton P. Korver, II, Orange City, Iowa

[73] Assignee: Med-Tec, Inc., Orange City, Iowa

[21] Appl. No.: 364,658

[22] Filed: Dec. 27, 1994

[51] Int. Cl.⁶ ............................................. A61N 5/10
[52] U.S. Cl. ................................. 378/65; 378/209
[58] Field of Search ............................ 378/209, 208, 378/65

[56] References Cited

U.S. PATENT DOCUMENTS

| | | | |
|---|---|---|---|
| 1,725,030 | 8/1929 | Wantz | 378/209 |
| 1,768,769 | 7/1930 | Kelley | 378/209 |
| 3,222,692 | 12/1965 | Shewchenko | 5/66 |
| 4,146,793 | 3/1979 | Bergstrom et al. | 378/161 |
| 4,991,243 | 2/1991 | Rottermann | 5/60 |
| 5,127,034 | 6/1992 | Wright | 378/209 |
| 5,239,716 | 8/1993 | Fisk | 5/630 |

FOREIGN PATENT DOCUMENTS 1435223  5/1976  United Kingdom.

*Primary Examiner*—Craig E. Church
*Attorney, Agent, or Firm*—Zarley, McKee, Thomte, Voorhees, & Sease

[57] ABSTRACT

A radiation table insert comprises a perimeter frame having at least one open side and a radiation transparent rigid grid mounted within said perimeter frame, to provide an oblique lateral treatment port along the open side of said frame. The open side of the carbon fiber grid is provided with a down-turned flange grid that provides the structural support to help prevent sag and to provide a radiotranslucent window that eliminates potential radiation build-up. This design is particularly important in meeting the challenges of arch or rational therapy programs that require later oblique treatment angles.

13 Claims, 3 Drawing Sheets

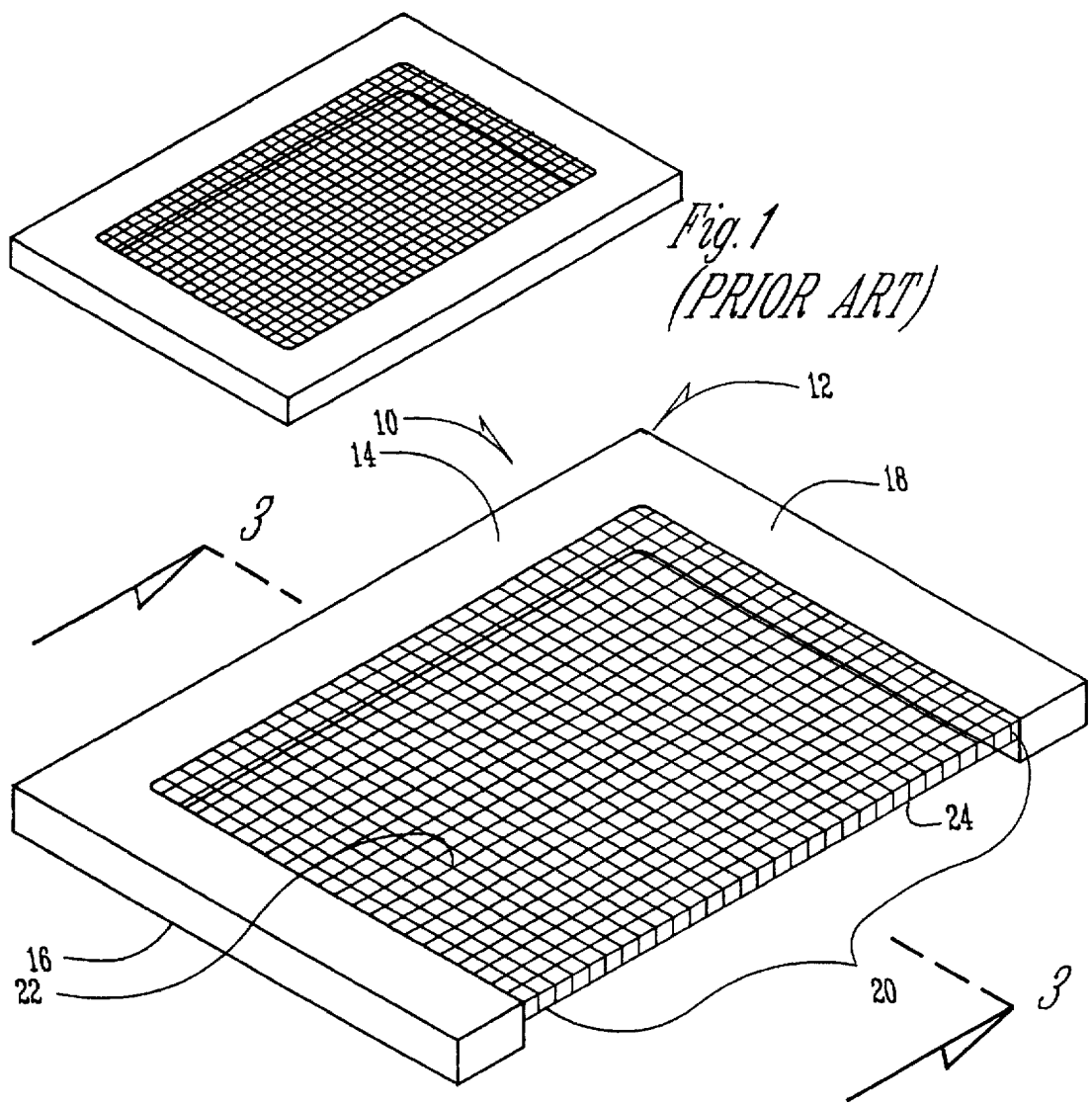
Fig. 1 (PRIOR ART)
Fig. 2
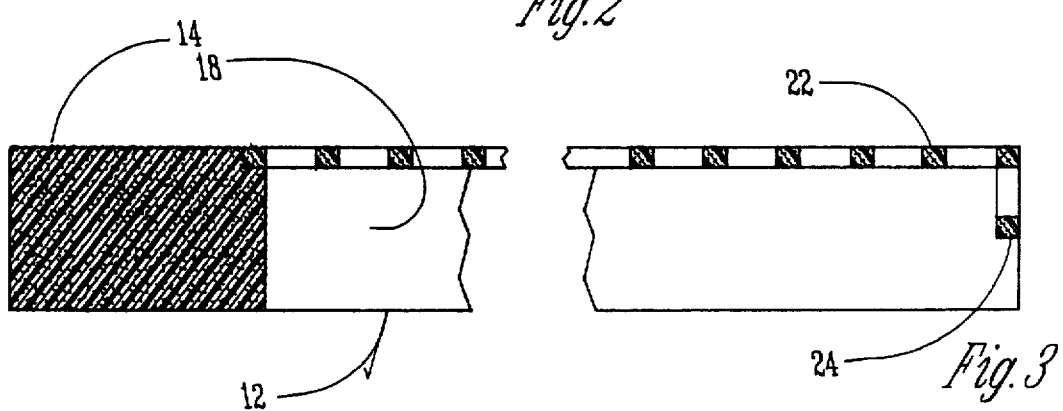
Fig. 3

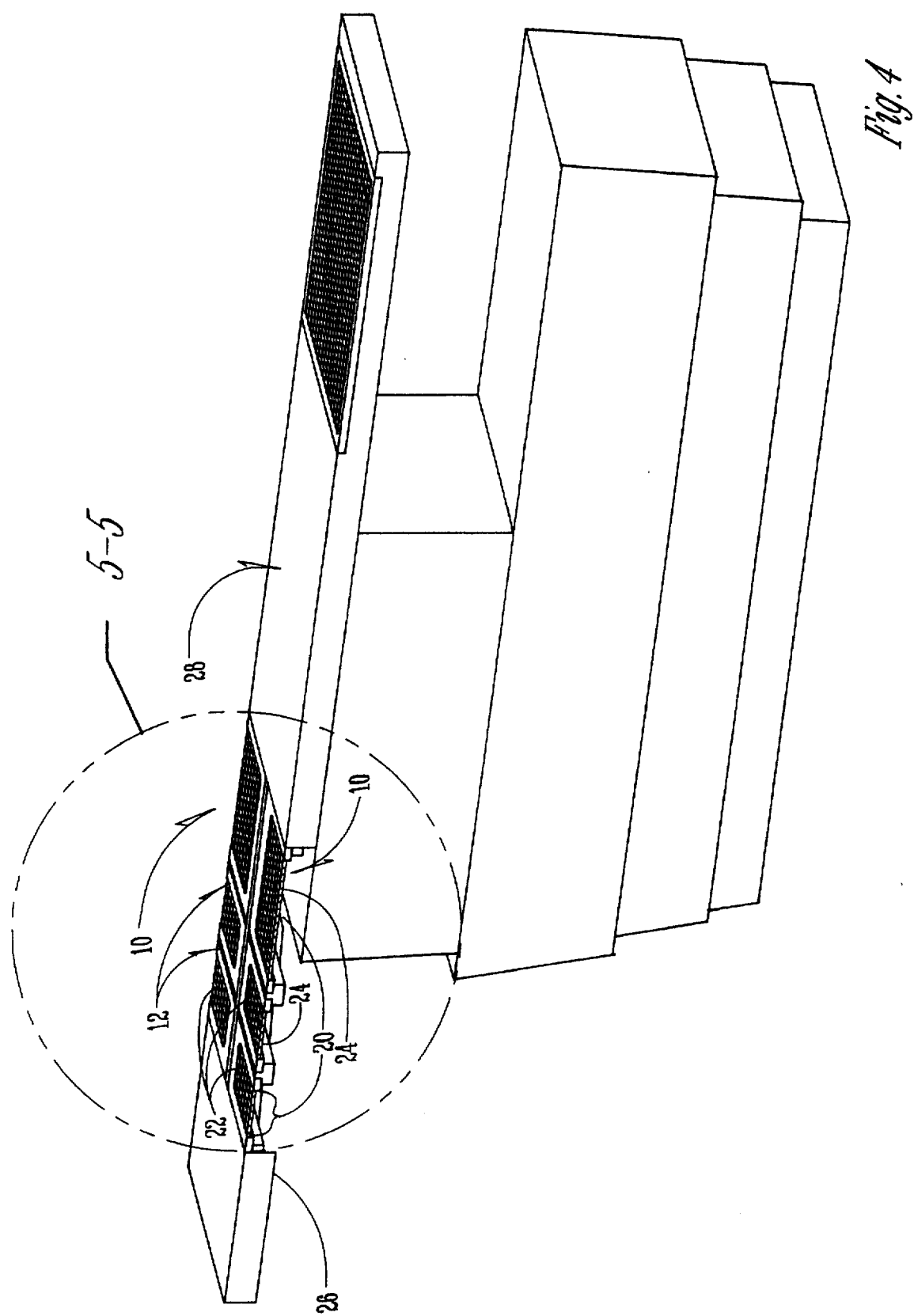

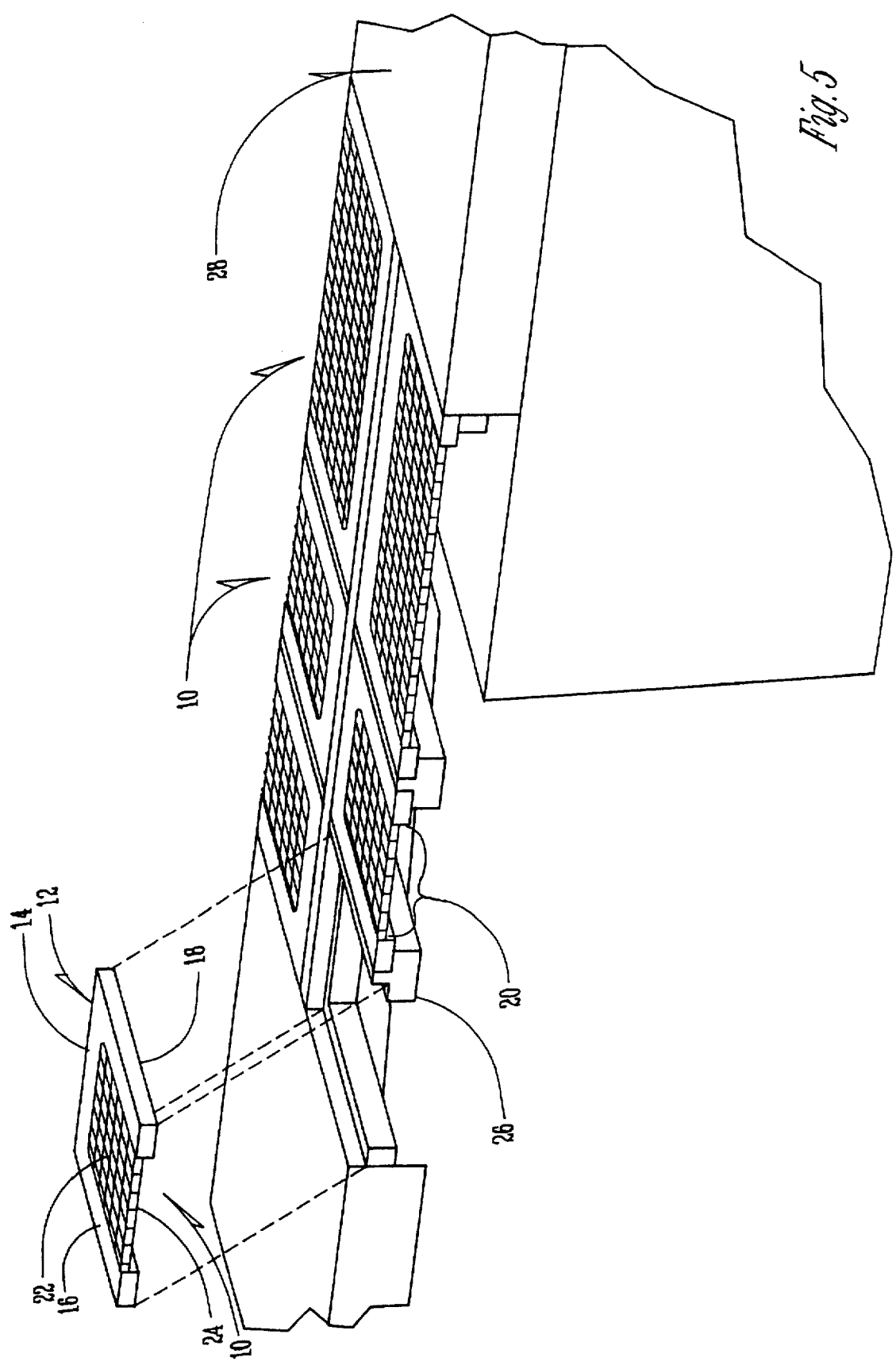

RADIATION THERAPY GRID FOR USE WITH TREATMENT COUCH

BACKGROUND OF THE INVENTION

The present invention relates to a radiation permeable table insert, used in the reclining surface of a patient's radiation therapy couch.

Radiation therapy couches are conventional and typically used to hold the patient in a substantially rigid position while the patient is being exposed to a radiation source. Typically the radiation source is mounted above the couch and movable around the couch so that the patient can be exposed to radiation from all possible angles, all to allow for purposefully directed radiation at the precise tumor site needed in order to destroy the tumor and minimize the exposure to healthy tissue.

Such treatment couches usually have open windows or frame supports at both ends providing a passageway for radiation to be directed through a table insert at the patient's tissue. This prevents having any of the radiation attenuated or absorbed by the couch itself. Typical radiation therapy couches are well known and are made by companies such as Siemen's.

It is important for the accuracy of calculations of the radiologist and the directional precision of the instrument that the patient's body is maintained in a rigid, properly aligned position. The correct alignment of the treatment rays must be maintained, otherwise needless harm to good body tissue may occur or dose attenuation may occur.

Currently manufacturers are supplied with rigid frames, often made of aluminum, to provide a four-sided framework with a grid, mounted in the frame similar to the way nylon strings are mounted in a tennis racket. This frame is then inserted into its proper window position in the radiation therapy couch. In this way there is a radiation transparent window in the couch.

Numerous problems exist with current frames as they are used. In the first instance those frames, if made of material such as aluminum, block some of the rays and may attenuate the radiation, making the dose inaccurate. This is especially true if the emitting apparatus is mounted in a position such that the emitted radiation is along a line that would normally pass through the framework of the tray.

In addition to the framework often blocking some of the emitted radiation, many of the materials used as the grid or network such as nylon will sag after a few uses. As a result the proper alignment of the patient with regard to the x-ray emitting apparatus, is no longer maintained.

Particularly troublesome in the current times when x-ray emitting patterns and doses are mathematically calculated for 3-dimensional treatments, various angles on the 360° position around the tumor point are often impossible to use since the couch insert frame itself blocks some of the dose if otherwise desired angle is used.

It therefore can be seen that there is a continuing need for development of radiation therapy table inserts that will not sag, that will maintain the body in a precise fixed position, and that will allow substantial freedom to the x-ray operator to orient the rays at as many angles as possible around 360° of the patient's tumor location. Also there is always a need for uninterfered lateral x-ray access. This invention has as its primary objective the fulfillment of these needs.

SUMMARY OF THE INVENTION

A radiation therapy table insert is provided in order to avoid the disadvantages of current table inserts. The insert comprises a perimeter frame having at least one open side, and a rigid radiation transparent stringing mounted within the perimeter frame to provide an unobstructed lateral treatment port along the open side of the frame. Preferably the stringing is made of carbon fiber, and if desired, the frame itself may be made of radiation transparent material such as carbon fiber. This will provide virtually 360° unobstructed capability of x-ray exposure.

In addition to the table insert, the invention also relates to the radiation table insert in combination with a radiation therapy couch.

BRIEF DESCRIPTION OF THE DRAWINGS

FIG. 1 is a perspective view of a prior art radiation therapy table insert.

FIG. 2 is a perspective view of the radiation therapy table insert of the present invention.

FIG. 3 shows a cross section of the insert along line 3–3 of FIG. 2.

FIG. 4 shows the insert mounted into the spine end of a conventional radiation therapy couch.

FIG. 5 shows an enlarged exploded view of the couch insert positions taken from lines 5—5 in FIG. 4.

DETAILED DESCRIPTION OF THE INVENTION

The radiation therapy table insert 10 is comprised of a U-shaped perimeter frame 12 having a base portion 14 and a pair of opposingly spaced frame members 16 and 18 to define a laterally open side opposite the base portion 14, here designated as 20. Frame member 12 may be made of rigid aluminum or in a preferred embodiment is made of a radiation transparent material such as a carbon fiber frame of a thickness of from about ½" to 1". Mounted within frame 12 is a rigid radiation transparent grid 22. The grid 22 needs to be a radiation transparent material, and preferably is a carbon grid. Nylon or Kevlar® string is woven under tension (like a tennis racket) and therefore could not make a flange. It is preferred that the stringing be a substantially rigid carbon fiber grid having ⅝th inch by ⅝th inch squares and ⅛th inch thick. The carbon fiber grid 22 is mounted to the frame 12, the interface of the grid 22 and frame 12 by any suitable mounting means, preferably by use of a carbon fiber adhesive such as Hysol® although other satisfactory adhesive materials may also be employed such as 3M Scotch-Weld 2216 BA Epoxy adhesive, Dexter Hysol EA 9430 epoxy adhesive, and other carbon fiber adhesives.

The carbon fiber grid is constructed by laying ⅛-inch wide carbon fiber ribbons, which are impregnated with a thermo-set resin, in a grid mold that positions the ribbons in an overlaid, intersecting pattern. Once the desired number of laminating ribbons is reached—which will provide the necessary thickness—a rubber "intensifier" or top plate is placed over the grid mold, and pressure and heat applied which compress and cure the fibers into a rigid grid structure.

As illustrated in FIG. 2 and 3, the perimeter edge of carbon fiber grid 22 is turned down at right angles to define edge 24 which defines the radiation transparent lateral treatment port.

FIG. 4 illustrates the table insert 10 mounted to the spine end 26 of a conventional radiation therapy table 28 (depicted is an illustration of a Siemen's table). As shown in FIG. 5 with table insert 10 of the present invention, there is an open lateral side along edge 24 as defined by carbon fiber grid flange 24. In this way there is complete lateral access. This is in contrast to conventional, closed frame table inserts which prevent access along the lateral side of the frame after insertion into a radiation therapy table at the spine end as illustrated in FIG. 4.

Certain constructional features are worthy of mention. It is preferred that the grid is a carbon fiber grid since such a grid is rigid, does not sag, and presents no concern about transmission of radiation, it being radiation transparent. It is also preferred that the frame 12 be made of carbon fiber material that is non-metallic and also radiation transparent. In this way, the ultimate radiation accessibility is for three dimensions (360°) around the patient. Thus the radiation therapist can shoot at low angles with minimum interference from both above and below the patient.

It therefore can be seen that the frameless side design provides a lateral treatment port, and if the frame itself is made of a carbon fiber material such as ½" to 1" thick compressed carbon material, then greater patient accessibility is provided from all angles. The invention therefore accomplishes at least all of its stated objectives.

What is claimed is:

1. In combination a radiation therapy couch for body support of a patient to be treated, and a radiation therapy couch insert comprising, a rigid perimeter frame having at least one open frame portion of said perimeter frame, and an independently rigid radiation transparent grid mounted to said perimeter frame so as to provide a lateral treatment port along said open frame portion of side perimeter frame wherein said frame provides primarily vertical support to the plane rather than lateral support.

2. The combination of claim 1 further comprising a carbon fiber grid flange along said open frame portion.

3. The combination of claim 1 wherein said perimeter frame is made of aluminum or carbon fiber.

4. The combination of claim 1 wherein said grid is a carbon fiber grid.

5. The combination of claim 1 wherein the perimeter frame is radiation transparent.

6. The combination of claim 2 wherein said flange is comprised of a portion of the grid disposed at a downward angle from the remainder of the grid.

7. The combination table insert and radiation therapy couch of claim 1 which has a carbon fiber grid flange along said open side.

8. The combination table insert and radiation therapy couch of claim 1 wherein said perimeter frame is made of aluminum.

9. The combination table insert and radiation therapy couch of claim 1 wherein said grid is a carbon fiber grid.

10. The combination table and radiation therapy couch of claim 1 wherein said perimeter frame is radiation transparent.

11. The combination of claim 1 further comprising a plurality of said radiation therapy couch inserts.

12. A method of providing near 360° accessibility of a patient's tumor site for radiation therapy, comprising:

providing a radiation transparent, rigid table insert comprised of an independently rigid grid disposed within an open-ended frame;

inserting into a radiation therapy couch the radiation transparent, rigid table insert; and thereafter administering radiation to said patient.

13. A radiation therapy table insert comprising:

a U-shaped frame;

a rigid, substantially nonflexible radiation transparent grid coupled to the U-shaped frame, said grid being substantially rigid independent of the U-shaped frame, said grid having four sides, three of said sides being coupled to the U-shaped frame, the fourth side being positioned along the open side of the U-shaped frame;

wherein a portion of the grid along the fourth side is positioned at an angle to the remainder of the grid forming a flange to provide additional strength to the grid.

\* \* \* \* \*